United States Patent [19]

Halperin et al.

[11] Patent Number: 5,533,964
[45] Date of Patent: Jul. 9, 1996

[54] APPARATUS FOR REMOVAL OF EXCESS HYDROGEN IONS FROM HUMANS

[75] Inventors: Mitchell L. Halperin, North York; Surinder Cheema-Dhadli, Mississauga, both of Canada

[73] Assignee: Rossmark Medical Publishers Inc., Ontario, Canada

[21] Appl. No.: 197,949

[22] Filed: Feb. 17, 1994

[51] Int. Cl.$^6$ .................................................. A61M 37/00
[52] U.S. Cl. .................. 604/4; 604/5; 604/190; 604/226
[58] Field of Search .................. 604/4, 5, 6, 190, 604/226, 236, 406; 424/424

[56] References Cited

U.S. PATENT DOCUMENTS

| | | | |
|---|---|---|---|
| 400,491 | 4/1889 | Ross | 604/226 |
| 3,953,329 | 4/1976 | Updike | 604/5 |
| 3,994,799 | 11/1976 | Yao et al. | 604/5 |
| 4,007,138 | 2/1977 | Kanig | 260/2.1 E |
| 4,435,176 | 3/1984 | Ishikawa | 604/190 |
| 4,878,891 | 11/1989 | Judy et al. | 604/5 |
| 5,019,096 | 5/1991 | Fox, Jr. et al. | 604/265 |

*Primary Examiner*—Paul B. Prebilic
*Attorney, Agent, or Firm*—Riches, McKenzie & Herbert

[57] ABSTRACT

A compound or composition incorporating silver carbonate is disclosed for use in removing excess hydrogen ions in a patient. The silver carbonate reacts with chloride ions which naturally occur in the patient's body fluids to produce a silver chloride precipitate. The chemical reaction producing silver chloride causes the release of hydroxyl, carbonate and/or bicarbonate ions which react with free hydrogen ions to form carbon dioxide and water. The silver carbonate compound or composition may be provided in a blood filtration cartridge, syringe or an orally ingestible form surrounded by a selectively permeable membrane. The membrane is selected to permit movement of ions, as well as carbon dioxide and water molecules therethrough, while preventing the silver carbonate or silver chloride precipitate from being released into the patient.

12 Claims, 2 Drawing Sheets

APPARATUS FOR REMOVAL OF EXCESS HYDROGEN IONS FROM HUMANS

SCOPE OF THE INVENTION

This invention relates generally to a novel compound or composition which may be used to remove excess hydrogen ions ($H^+$) from a patient. Excess hydrogen ions are generated in the patient, in response to such conditions as heart attack, renal failure and other medical conditions and can cause further damage to the patient. More particularly, the invention relates to a composition which releases hydroxyl, carbonate and/or bicarbonate ions which will react with the excess free hydrogen ions to produce $H_2O$ and $CO_2$ as the sole by-products. The present inventors have discovered that by the use of $Ag_2CO_3$ as a compound or in a composition, the silver ions ($Ag^+$) bond with the free chloride ions ($Cl^-$) to release carbonate ions ($CO_3^=$) which then bind with the free excess hydrogen ions ($H^+$), without introducing potentially harmful cations or anions to the patient.

BACKGROUND OF THE INVENTION

Excess hydrogen ions ($H^+$) are generated in an individual as a result of a heart attack, acute renal failure or other maladies, and have a serious and deleterious affect on the individual's health.

The conventional treatment in removing such excess of hydrogen ions ($H^+$) involves the administration of sodium bicarbonate ($NaHCO_3$) or sodium carbonate ($Na_2CO_3$), alone or in combination. The carbonate ($CO_3^=$) and bicarbonate ions ($HCO_3^-$) react with free hydrogen ions ($H^+$) to produce $H_2O$ and $CO_2$, but also release at the same time, free sodium ions ($Na^+$). A major disadvantage of the conventional administration of sodium bicarbonate to reduce the number of free hydrogen ions ($H^+$) is that the amount of $NaHCO_3$ or $Na_2CO_3$ which can be safely administered is limited, because free sodium ions ($Na^+$) in large concentrations or content may be harmful to the patient.

HEART ATTACK PATIENTS

The human body needs adenosinetriphosphate (ATP) as useful energy so that the body can perform biologic work. To permit this work, ATP must be converted to adenosinediphosphate (ADP), lactate anions ($L^-$) and hydrogen ions ($H^+$). In a healthy individual, the body's regeneration of needed ATP predominantly occurs by the consumption of oxygen ($O_2$) through the tricarboxylic acid (TCA) cycle and the electron transport pathway (ETP), as for example, is described at pages 215 to 222 of *Clinical Detective Stories*, Halperin, M. L. and Rolleston, F. S., Portland Press, 1993. The TCA cycle oxidizes acetyl groups (found in acetyl-CoA) to yield the useful products NADH (nicotinamide adenine dinucleotide ($AND^+$) having a hydrogen ion ($H^+$) bound thereto) and $FADH_2$ (flavine adenine dinucleotide), and the ETP oxidizes the hydrogen atoms in the NADH or $FADH_2$ molecule to form $H_2O$, with the production of ATP.

Acute episodes of heart disease lead to the rapid deterioration and eventual death of a patient when the heart fails to pump enough oxygenated blood to vital organs. Hypoxia, a deficiency of oxygen reaching these vital organs of the body, forces tissues to regenerate their ATP from anaerobic glycolysis (the conversion of glucose to lactic acid ($L^-+H^+$)) Anaerobic glycolysis yields two molecules of ATP plus two molecules of lactic acid ($L^-+H^+$) per molecule of glucose consumed. As such, hypoxia causes the rapid formation of lactic acid ($L^-+H^+$) and prevents the oxidation of the hydrogen atoms on NADH to yield ATP.

Complete oxidation of glucose to $CO_2$ and $H_2O$ via glycolysis, pyruvate dehydrogenase (PDH), and the ATP generation system yields 36 to 40 ATP per glucose. Anaerobic glycolysis must therefore use glucose 18 to 20 times faster than complete oxidation to meet the normal demands of a tissue for regeneration of ATP. As such, this pathway produces hydrogen ions ($H^+$) at a very rapid rate.

To keep a patient having a heart attack alive long enough to allow for more formal intervention, an alkali is administered to offset the hydrogen ion ($H^+$) build up. Typically, alkaline salts composed of a sodium cation ($Na^+$) together with a $H^+$ acceptor, such as bicarbonates ($HCO_3^-$), carbonates ($CO_3^=$), hydroxyl ions ($OH^-$) or other $H^+$ acceptors.

ACUTE RENAL FAILURE

Patient's experiencing acute renal failure, may also develop excessive levels of hydrogen ions ($H^+$) in their bodies. The kidneys act to eliminate from the body in rank order, potassium ions ($K^+$), hydrogen ions ($H^+$) and sodium ions ($Na^+$).

CONVENTIONAL TREATMENT $NaHCO_3$ is by far most widely used as a treatment to remove excess hydrogen ions, which on implementation results in the following chemical reaction:

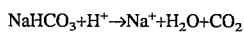

$$NaHCO_3 + H^+ \rightarrow Na^+ + H_2O + CO_2$$

By the administration of conventional treatments, excess amounts of $Na^+$ ions are introduced into the patient. $Na^+$ ions are particularly disadvantageous as sodium tends to pool in the fluid outside cells, and of special importance in the patient's lungs, and if present in sufficiently large amounts, may lead to death.

As a practical matter therefore, there are limits to the amount of $NaHCO_3$ (or other conventional buffering compositions) which may be safely administered. The net result is a corresponding limit to the concentration of free hydrogen ions ($H^+$) which may be safely removed.

SUMMARY OF THE INVENTION

It is therefore an object of the invention to provide a compound or composition which acts to bind excess free hydrogen ions ($H^+$) which occur in a patient as a result of heart attack, acute renal failure or other medical condition, and which when administered, does not introduce quantities of cations which may produce a particular disadvantage to the patient.

Another objective of the invention is to provide a compound or composition which substitutes a bicarbonate, carbonate or hydroxyl ion for chloride ions ($Cl^-$) which naturally occur throughout the patient's body.

A further object of the invention is to provide a composition which binds with free hydrogen ions ($H^+$) to produce $H_2O$ and $CO_2$, and which leaves substantially no undesired residue in the patient.

A further object of the invention is to provide an apparatus or kit for use in filtering and removing excess $H^+$ ions from a patient's body which does not alter the cation composition of the body.

In accordance with the present invention, the applicant has discovered that the compound $Ag_2CO_3$ or $Ag_2CO_3$ as part of a composition in solid form may be advantageously used to reduce the concentration of free hydrogen ions ($H^+$) in a patient without introducing harmful excess cations.

By providing $Ag_2CO_3$ in solid form, the silver cation $Ag^+$ from the solid or composition is found to react avidly and specifically with chloride ions ($Cl^-$) which naturally occur in the patient's body under the reaction:

$$2Cl^- + Ag_2CO_3 \rightarrow 2AgCl + CO_3^= \qquad (i)$$

The carbonate ion ($CO_3^=$) freed by this reaction then bonds with free excess hydrogen ions ($H^+$) in the patient's fluids by the chemical reaction:

$$CO_3^= + H^+ \rightarrow HCO_3 \qquad (ii)$$

and $$HCO_3^- + H^+ \rightarrow H_2O + CO_2 \qquad (iii)$$

Silver has not previously been considered for use in compositions/compounds out of concern that free silver ions ($Ag^+$) introduced into the patient may be deleterious to the patient's health. The applicant has discovered however, that with the compound/composition of the present invention, free silver ions ($Ag^+$) bind with free chloride ions ($Cl^-$) derived from a patient's body to form a highly insoluble silver chloride precipitate which does not adversely affect the patient.

As the AgCl has an extremely low soluability, it exists almost entirely as a solid precipitate with virtually no free silver ions ($Ag^+$) released into the patient. Free hydrogen ions ($H^+$) in the patient combine with the released carbonate ($CO_3^-$) or hydrogen carbonate ($HCO_3^-$) ions, yielding water and carbon dioxide, with no increase in excess cations in the patients.

In another embodiment, a composition comprising resin and $Ag_2CO_3$ is used in place of simply the solid $Ag_2CO_3$ compound/composition. The resin is preferably an anion exchange resin, as for example Dowex −1 (ionic form $OH^-$) or Dowex macroporous (ionic form $OH^-$, $CO_3^=$ or $HCO_3$). The patient's blood, plasma or body fluids may be extracted through a selectively permeable membrane and passed through the ion exchange resin. As free chloride ions ($Cl^-$) naturally present in the plasma or fluids bond with the silver ions ($Ag^+$) or with the resin, carbonate ions ($CO_3^=$), bicarbonate ions ($HCO_3^-$) and/or hydroxyl ions ($OH^-$) are released into the plasma or fluids under the reactions:

$$2Cl^- + Resin.CO_3 \rightarrow Resin.Cl + CO_3^= \qquad (iv)$$

$$Cl^- + Resin.HCO_3 \rightarrow Resin.Cl + HCO_3^- \qquad (v)$$

$$Cl^- + Resin.OH \rightarrow Resin.Cl + OH^- \qquad (vi)$$

The carbonate ions ($CO_3^=$), or bicarbonate ions ($HCO_3^-$) then react with free hydrogen ions ($H^+$) as previously described in reactions (ii) and (iii) producing water and carbon dioxide. Hydroxyl ions ($OH^-$) react with free hydrogen ions ($H^+$) to produce water by the reaction:

$$OH^- + H^+ \rightarrow H_2O \qquad (vii)$$

In a further embodiment, the composition resin/$Ag_2CO_3$ or solid $Ag_2CO_3$ compound may be provided for oral ingestion, for ion exchange within the gastrointestinal tract. Preferably such a compound or composition would be provided within a selectively permeable membrane which would allow substantially unhindered transmission of fluids together with $Cl^-$, $CO_3^=$, $OH^-$, and $HCO_3^-$ ions therethrough.

Accordingly in one aspect the present invention resides in either a buffering compound which comprises $Ag_2CO_3$ or a composition which comprises solid $Ag_2CO_3$ and a carrier.

In another aspect the present invention resides in a kit for use in buffering excess hydrogen ions in a patient, the kit comprising either a buffering compound comprising $Ag_2CO_3$ or a buffering composition comprising $Ag_2CO_3$ with or without a resin, and means for selectively permitting ion flow between a patient's body fluid and the buffering compound or composition while preventing movement of the buffering compound into the fluid.

In another aspect the present invention resides in an apparatus for use in buffering excess hydrogen ions in a patient's blood, the apparatus comprising a housing having a reaction chamber and a blood chamber, the reaction chamber separated from the blood chamber by a membrane, a buffering compound comprising $Ag_2CO_3$ disposed in the reaction chamber, wherein the membrane is selectively permeable to permit the passage of free ions therethrough while preventing movement of said compound, plasma proteins and red blood cells thereacross.

In a further aspect the present invention resides in a syringe or cartridge for use in buffering excess hydrogen ions in a patient's blood, the syringe comprising a housing having a reaction chamber and a blood chamber, said reaction chamber separated from said blood chamber by a membrane disposed across said housing, a buffering composition comprising $Ag_2CO_3$ and a resin disposed in the reaction chamber, the membrane selectively permeable to permit the movement of free ions therethrough while preventing movement of said composition, plasma proteins and red blood cells thereacross, means for drawing a quantity of blood into the blood chamber and then reintroducing the blood into said patient.

In another aspect the membrane is preferably a natural cellulose membrane.

DETAILED DESCRIPTION

Figure 1:
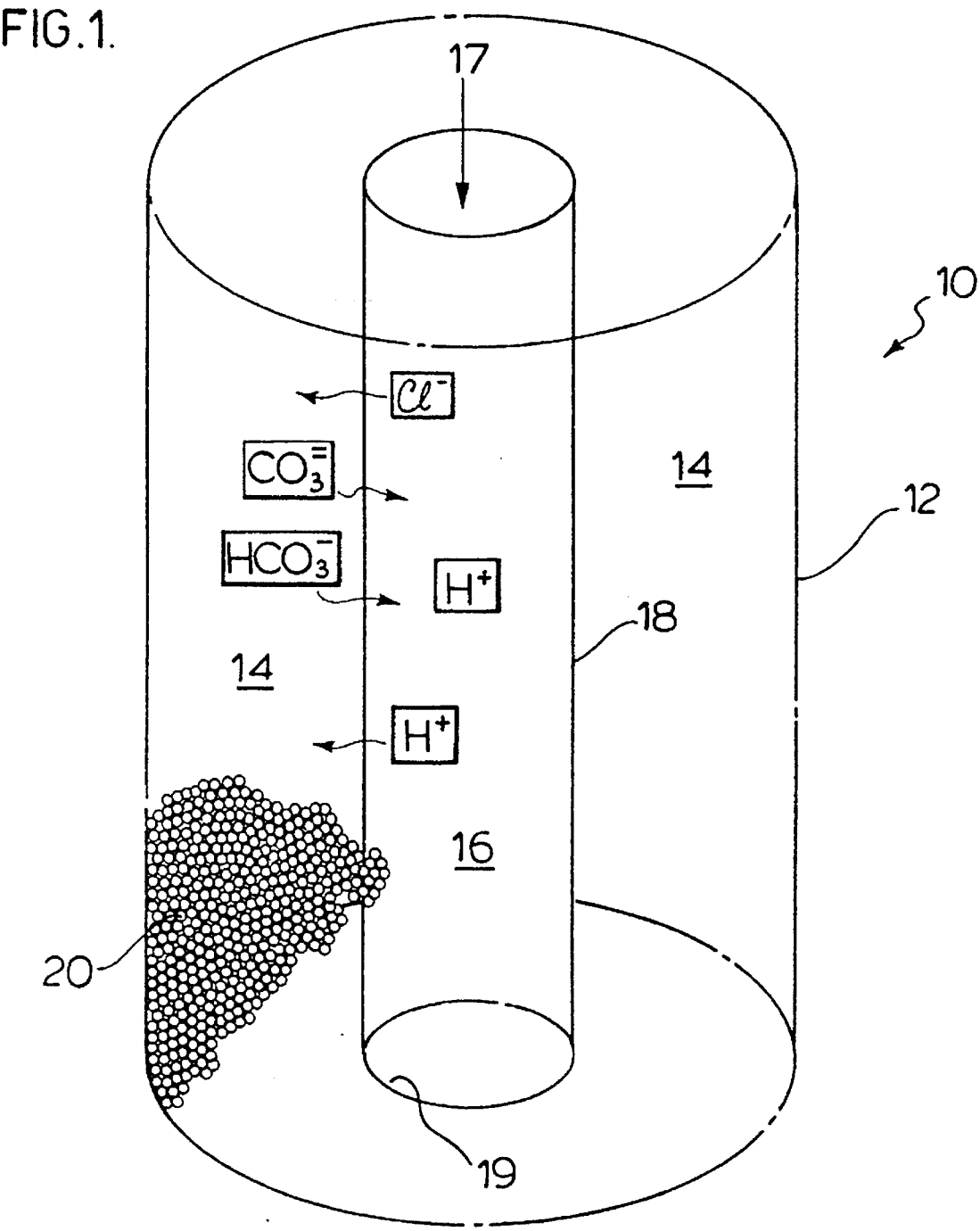
FIG. 1 is a schematic view of a filter cartridge for use in accordance with a first aspect of the invention.

It has been discovered that either a compound or composition comprising $Ag_2CO_3$ in solid form may advantageously be used to treat patients having unduly high concentrations of hydrogen ions ($H^+$) in their body as a result of heart attack, acute renal kidney failure or other medical conditions.

The applicants have found, that on contacting body fluids with $Ag_2CO_3$, free chloride ions ($Cl^-$) present naturally in the body fluids advantageously combine with silver ions ($Ag^+$) which exist in an almost instantaneous equilibrium with the solid $Ag_2CO_3$ to produce a solid precipitate by the reaction:

$$2Cl^- + Ag_2CO_3 \rightarrow 2AgCl + CO_3^= \qquad (i)$$

The carbonate ion ($CO_3^=$) released by the reaction bond with free hydrogen ions ($H^+$) in the patient's fluids by the reactions:

$$H^+CO_3^= \rightarrow HCO_3^- \quad (ii)$$

and $$H^+ + HCO_3^- \rightarrow H_2O + CO_2 \quad (iii)$$

By reactions (ii) and (iii) the molar concentration of free hydrogen ions ($H^+$) in the patient may be reduced by binding the hydrogen ions in water molecules. Further, as the silver cation ($Ag^+$) bonds with free chloride ions ($Cl^-$) aggressively to form a precipitate, harmful concentrations of free silver cations ($Ag^+$) are not introduced into the patient.

$Ag_2CO_3$ is particularly suitable for the present invention as $Ag_2CO_3$ exists in equilibrium with a very fast and almost simultaneous existence with free $Ag^+$ ions and $CO_3^=$ ions. As such, free silver ions ($Ag^+$) tend to bond almost immediately with either chloride ions ($Cl^-$) or carbonate ions ($CO_3^=$), or bicarbonate ions ($HCO_3^-$).

$Ag_2CO_3$ has an extremely low solubility in water of less than 0.0032 grams/100 cc in cold water. Once the silver ions ($Ag^+$) have bonded with $Cl^-$ ions, the resulting AgCl forms a solid precipitate having a still lower solubility of less than 0.000089 grams/100 cc in cold water. As such, by the use of $Ag_2CO_3$ there is minimal likelihood that free silver ions ($Ag^+$) would exist in solution so as to adversely affect the patient's health. The lower solubility of the resulting precipitate AgCl advantageously reduces the likelihood of the reaction reversing to free chloride ions ($Cl^-$) and silver ions ($Ag^+$) once the AgCl precipitate has formed.

The insolubility of the resulting precipitate further advantageously permits the use of the $Ag_2CO_3$ compound or composition with selectively permeable membranes, and preferably membranes which permit the passage therethrough of small molecular weight compounds and not larger molecular compounds.

While $Ag_2CO_3$ as a solid compound or composition may be used to achieve the objects of the present invention, $Ag_2CO_3$ in other forms may also be used. $Ag_2CO_3$ may be provided as part of a composition together with a carrier. In one embodiment the carrier preferably is an ion exchange resin which incorporates $Ag_2CO_3$. Plasma or other fluids from a patient, may be contacted with the resin/$Ag_2CO_3$ composition. On contact, chloride ions ($Cl^-$) in the body fluids bond with silver ions ($Ag^+$) present in the resin by the reaction:

$$Cl^{-\,Resin.HCO_3} \rightarrow Resin.Cl + HCO_3^- \quad (iv)$$

the bicarbonate ion ($HCO_3^-$) then binds with free hydrogen ions ($H^+$) in the patient's body fluids to reduce the molar concentration of free hydrogen ions by the reaction:

$$H^+ + HCO_3^- \rightarrow H_2O + CO_2$$

Resins particularly suitable for use with the present invention include anion exchangers on dextran, anion exchangers on agarose, anion exchangers on cellulose, and anion exchangers on polystyrene, such as those sold under the trade names Dowex anion exchangers.

In another embodiment the $Ag_2CO_3$ composition, either alone or in combination with a resin or other suitable carrier, is encapsulated within a carrier, such as a selectively permeable membrane. The selectively permeable membrane is chosen to permit the transmission of ions therethrough while preventing the passage of solid $Ag_2CO_3$ or the resulting precipitate AgCl therethrough. Suitable selectively permeable membranes include pure regenerated natural cellulose membranes, such as those sold under the trade name Spectra/Por membranes.

As is to be appreciated, as buffering carbonate ($CO_3$) or bicarbonate ions ($HCO_3^-$) are released on the silver ions ($Ag^+$) bonding with chloride ions ($Cl^-$) to form the highly insoluble precipitate AgCl, almost no free cations are released by the reactions. As such by the use of the present invention buffering ions may be provided to bond with hydrogen ions ($H^+$) with virtually no increase in harmful cations such as $Na^+$ in the patient.

While a resin has been disclosed as a component of a preferred composition, it is to be appreciated that other carriers may equally be used.

There are several possible uses for the compound or composition of the present invention in the treatment of patients. The following are provided by way of example only, and are not intended to be limiting.

EXAMPLE 1

Heart Attack Patients

The present invention may advantageously be used in the treatment of heart attack patients.

Where a patient has undergone a heart attack and oxygenated blood is no longer circulating, solid $Ag_2CO_3$ as either a compound or in a resin composition form may be used to reduce free hydrogen ions ($H^+$) in the patient's body, and provide a longer period of time in which other medical strategies to restart the heart may be taken.

A first embodiment of an apparatus for use with a compound comprising $Ag_2CO_3$ is best shown in FIG. 1.

FIG. 1 shows a blood filtration cartridge 10 characterized by a fluid impermeable chemically inert plastic outer housing 12. The interior of the housing 12 is divided into essentially two areas, a reaction chamber 14, and a centrally disposed blood passage chamber 16. The reaction chamber 14 is delineated from the blood passage chamber 16 by a selectively permeable membrane 18. A reactant compound 20 comprising $Ag_2CO_3$ is provided in the reaction chamber 14.

The selectively permeable membrane 18 is chosen to permit free passage of water and ions from the blood to move across the membrane 18 into and from the reaction chamber 14. The membrane 18 is further selected to prevent the movement of blood cells and proteins from the blood passage chamber 16 into the reaction chamber 14, or the movement of solid $Ag_2CO_3$ or the resulting AgCl precipitate from the reaction chamber 14 into the blood passage chamber 16.

In use, blood from a patient is extracted and pumped by a pump (not shown) through the cartridge 10 via passage inlet 17. As the blood enters the passage 16, the aqueous phase of blood containing chloride ions ($Cl^-$) and hydrogen ions ($H^+$) selectively pass through the membrane 18 into the reaction chamber 14. In the reactive chamber 14, buffering ions are freed on the chloride ions ($Cl^-$) forming a preferential bond with free silver ions ($Ag^+$) existing in rapid equilibrium with $Ag_2CO_3$. The result of the chloride ions ($Cl^-$) bonding with free silver ions ($Ag^+$) is the formation of the substantially insoluble precipitate AgCl in the reaction chamber 14 by the reaction:

$$Ag_2CO_3 + 2Cl^- \rightarrow 2AgCl + CO_3^= \quad (i)$$

As the chloride ions ($Cl^-$) bond with any available free silver ions ($Ag^+$), buffering carbonate ions ($CO_3^=$) and bicarbonate ions ($HCO_3^-$) are released. These released buffering ions either bond with free hydrogen ions ($H^+$) in the aqueous phase of the blood which has passed into the reaction chamber 14, or move through the membrane 18 into the blood passage chamber 16 to bond with free hydrogen ions ($H^+$) in the patient's blood by the reactions:

$$CO_3^= + H^+ \rightarrow HCO_3^- \qquad \text{(ii)}$$

and $$HCO_3^- + H^+ \rightarrow H_2O + CO_2 \qquad \text{(iii)}$$

In this manner, the concentration of free hydrogen ions ($H^+$) in the patient's blood can be reduced with virtually no potentially harmful cations being introduced into the patient's blood.

The treated blood is then pumped outwardly from the cartridge 10, via passage outlet 19 for reintroduction into the patient.

The removal of hydrogen ions ($H^+$) occurs in a 1:1 stoichiometric ratio with $HCO_3^-$ or OH ions and a 2:1 stoichiometric ratio with $CO_3^{2-}$ ions. As such, a given amount of $Ag_2CO_3$ will yield a particular "dosage" for removing a given concentration of hydrogen ions ($H^+$). In this manner a given quantity of $Ag_2CO_3$ may be provided in the cartridge 10 to buffer a given concentration of hydrogen ions ($H^+$).

Figure 2:
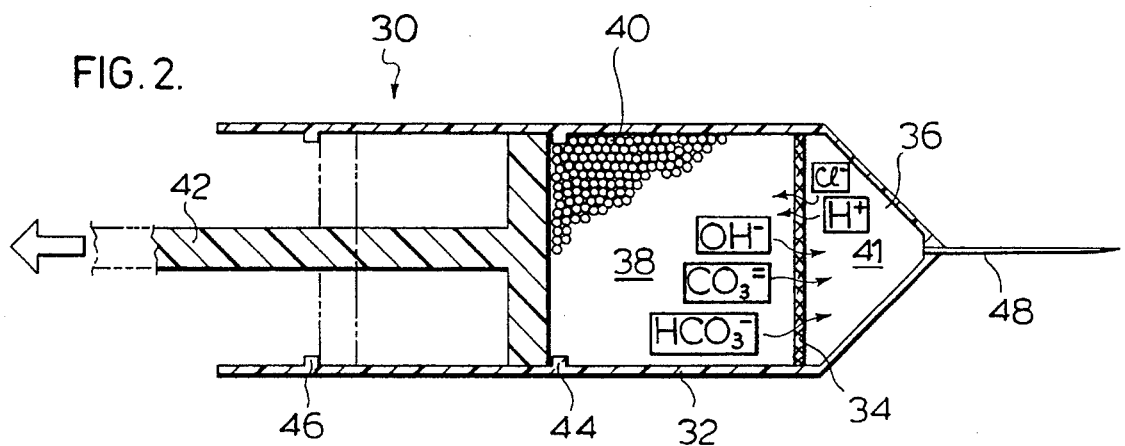
FIG. 2 is a schematic view of a syringe for use in accordance with a second aspect of the invention.

Reference may be made to FIG. 2 which shows a second embodiment of the invention. FIG. 2 shows a syringe 30 adapted for portable use in buffering free hydrogen ions ($H^+$) from a heart attack patient's blood 41. The syringe 30 is particularly suited for field use, as for example by a paramedic, prior to the patient's arrival at a hospital.

The syringe 30 is constructed on the same principles as the cartridge 10 shown in FIG. 1. The syringe 30 comprises a chemically inert housing 32, plunger 42 and needle 48. The syringe housing 32 is divided by a selectively permeable membrane 34 to delineate a blood chamber 36 and a reaction chamber 38. Microencapsulated reactant 40 is provided within the reaction chamber 38. The reactant 40 preferably is a composition comprising $Ag_2CO_3$ and a resin.

The membrane 34 is chosen to selectively prevent red blood cells and plasma proteins in blood 41 which has been drawn into the syringe 30 to pass therethrough into a reaction chamber 38, while permitting passage of water and ions thereacross.

Inner and outer annular stop rings 44,46 may be provided about the inner surface of the syringe housing 32 to limit inward and outward axial sliding of the plunger 42. The inner stop ring 44 advantageously acts to prevent the plunger 42 from being slid too far inwardly into the housing 32. Inward movement of the plunger 42 is limited to prevent the solid reactant 40 from being forced into contact with the membrane 34, whereby the membrane 34 may be damaged and reactant 40 may move into the blood chamber 36 or the patient. Outer annular flange 46 advantageously prevents the inadvertent complete withdrawal of the plunger 42 from the housing 32.

Although not essential, the interior of the syringe 36 may be maintained under a vacuum or filled with sterile isotonic saline so as to minimize the possibility of introducing air bubbles into the patient's blood.

In operation of the syringe 30, the needle 48 is inserted into a patient, and the plunger 42 is slid outwardly from the syringe housing 32, drawing a quantity of blood 41 into the blood chamber 36. As blood 41 is drawn from the patient, water, free chloride ions ($Cl^-$) and hydrogen ions ($H^+$) in the blood pass through the membrane 34 into the reaction chamber 38.

In the manner previously described with reference to FIG. 1, chloride ions ($Cl^-$) from the patient which have moved into the reaction chamber 38 bond with free silver ions ($Ag^+$) to produce an insoluble AgCl precipitate. As the free silver ions ($Ag^+$) bond with the chloride ions ($Cl^-$), carbonate ions ($CO_3^=$), hydroxyl ($OH^-$) ions or bicarbonate ions ($HCO_3^-$) are released. By reactions (ii), (iii) or (vii) described previously, the bicarbonate ($HCO_3^-$), hydroxyl ($OH^-$) and carbonate ions ($CO_3^=$) bond with either free hydrogen ions ($H^+$) which have passed through the membrane 34 into the reaction chamber 38, or themselves pass through the selectively permeable membrane 34 to bond with hydrogen ions ($H^+$) in the blood chamber 36.

The treated blood 41 having a reduced concentration of free hydrogen ions ($H^+$) and any remaining free buffering ions ($CO_3^=$, $OH^-$, $HCO_3^-$) may then be reintroduced into the patient by sliding the plunger 42 axially inwardly to a position abutting the stop ring 44.

The syringe 30 may contain a sufficiently large amount of microencapsulated reactant 40, such that in use, the plunger 42 may be repeatedly moved to withdraw, treat and then reinject blood 41 into a patient.

EXAMPLE 2

Kidney Patients

The compound of the present invention may be used inter vivos to reduce undesirable concentrations of excess free hydrogen ions ($H^+$) in patients who have experienced acute renal failure.

As the human stomach secretes naturally both hydrogen ions ($H^+$) and chloride ions ($Cl^-$), it is possible to provide for oral ingestion either a compound or composition comprising $Ag_2CO_3$.

Figure 3:
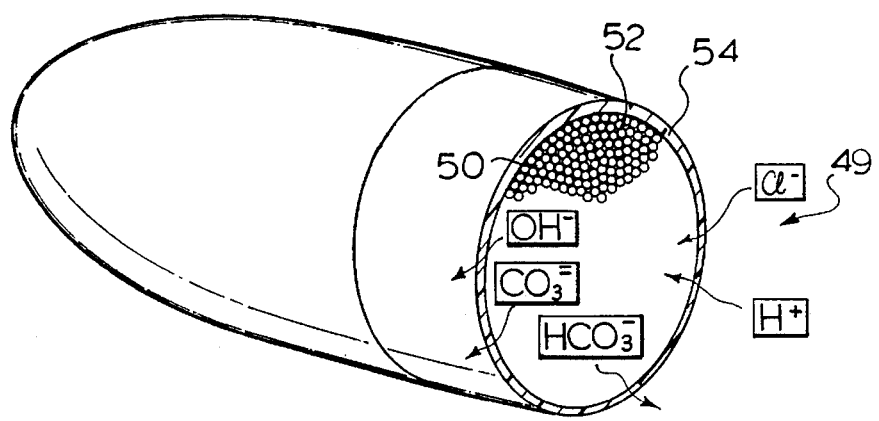
FIG. 3 is a cut-away perspective view of a capsule for use in accordance with a third aspect of the invention.

To remove excess hydrogen ions ($H^+$), a quantity of $Ag_2CO_3$ is ingested either as a solid compound, or more preferably and seen in FIG. 3, as a capsule 49 of solid reactant 50 comprising $Ag_2CO_3$ microencapsulated within a resin 52. The outer surface of the capsule 49 containing the reactant 50 preferably comprises a selectively permeable membrane 54, chosen to permit the movement of water, carbon dioxide and ions therethrough, while preventing the passage of the reactant 50 or the resulting solid precipitate AgCl.

Once orally ingested, chloride ions ($Cl^-$) and hydrogen ions ($H^+$) present in the patient's gastrointestinal tract pass through the membrane 54. The chloride ions ($Cl^-$) bond with free silver ions ($Ag^+$) to produce the precipitate AgCl by formula (i) disclosed previously. Bicarbonate ($HCO_3^-$), hydroxyl ($OH^-$) ions and carbonate ($CO_3^=$) ions released on the chloride ions ($Cl^-$) bonding with the silver ions ($Ag^+$), bond with free hydrogen ions ($H^+$) within the capsule 49 or pass outwardly through the membrane 54 to bond with free hydrogen ions ($H^+$) in the gastrointestinal tract to produce $CO_2$ and/or $H_2O$ (formulas (ii), (iii) and (vi) disclosed previously).

The combination of $Ag_2CO_3$ plus an anion exchange resin may further be used to permit the removal of unwanted ions such as sulfate ($SO_4^=$) and phosphate ($HPO_4^=$) in patients with kidney diseases or those lacking kidneys, for example by the reactions:

$$\text{Resin.}CO_3^= + SO_4^= \rightarrow \text{Resin.}SO_4^= + CO_3^= \qquad \text{(viii)}$$

$$\text{Resin.}CO_3^= + HPO_4^= \rightarrow \text{Resin.}HPO_4^= + CO_3^= \qquad \text{(ix)}$$

The $Ag_2CO_3$ composition for the treatment of kidney patients is still more preferably used in combination with existing treatments, such as those used to bond free potassium ions (K$^+$). For example, one known treatment used to bond free K$^+$ ions is presently marketed under the trade mark K-EXALATE. The composition of the present invention may be combined with treatments for binding K$^+$ ions to both reduce the concentrations of free hydrogen ions (H$^+$) and to improve the operation of potassium binders which by their operation release hydrogen ions (H$^+$).

Insofar as the composition for the present invention acts to bind free hydrogen ions (H$^+$) in a one-to-one stoichiometric ratio, it is possible to calculate the dosage or amount by weight of $Ag_2CO_3$ required to move a given molar quantity of excess hydrogen ions (H$^+$). It is therefore possible for an individual undergoing dialysis to calculate that X amount of $Ag_2CO_3$ should be ingested orally (or alternately rectally) on consuming 50 milliliters of wine, etc. as a counterbalance to an expected increase in hydrogen ions.

Although the disclosure describes and illustrates preferred embodiments and examples of the invention, the invention is not so limited. Many variations and modifications will now occur to those skilled in the art. For a definition of the invention reference may be made to the appended claims.

The embodiments of the invention in which an exclusive property or privilege is claimed are defined as follows:

1. A kit for reducing hydrogen ions in a patient's body fluid, said kit including, a buffering compound comprising $Ag_2CO_3$ in solid form for bonding with free cloride ions naturally present in said body fluid and substituting therefor buffering ions selected from the group consisting of carbonate ions and bicarbonate ions, and means for selectively permitting ion flow between the patient's body fluid and said buffering compound while preventing movement of said buffering compound into said patient, wherein in use, said buffering ions bond with said hydrogen ions to produce water and carbon dioxide molecules.

2. A kit for use in buffering excess hydrogen ions in a patient, said kit comprising, a buffering composition comprising a resin and $Ag_2CO_3$ for bonding with free chloride ions naturally present in the patient and substituting therefor buffering ions selected from the group consisting of carbonate ions and bicarbonate ions, and means for selectively permitting ion flow between a patient's body fluid and said buffering composition while preventing movement of said buffering composition into said patient, wherein in use, said buffering ions bond with said hydrogen ions to produce water and carbon dioxide molecules.

3. A kit as claimed in claim 1 wherein said fluid comprises blood, said kit further comprising, means for extracting a quantity of said blood from a patient for buffering by said compound, and means for reintroducing buffered blood into said patient.

4. A kit as claimed in claim 1 wherein said means for selectively permitting ion flow comprises a selectively permeable membrane.

5. A kit as claimed in claim 4 wherein said membrane is a natural cellulose membrane.

6. A kit as claimed in claim 2 wherein said fluid comprises blood, said kit further comprising, means for extracting a quantity of said blood from a patient for buffering by said composition, and means for reintroducing buffered blood into said patient.

7. A kit as claimed in claim 2 wherein said means for selectively permitting ion flow comprises a selectively permeable membrane.

8. A kit as claimed in claim 7 wherein said membrane is a natural cellulose membrane.

9. A kit as claimed in claim 8 wherein said resin is selected from the group consisting of an anion exchanger on dextran, an anion exchanger on agarose, an anion exchanger on cellulose and an anion exchanger on polystyrene.

10. An apparatus for use in buffering excess hydrogen ions in a patient's blood, said apparatus comprising, a housing having a reaction chamber and a blood chamber, a hydrogen ion buffering compound comprising $Ag_2CO_3$ disposed in said reaction chamber, said buffering compound for bonding with free chloride ions naturally present in said blood and substituting therefor buffering ions selected from the group consisting of carbonate ions and bicarbonate ions, and said reaction chamber separated from said blood chamber by a membrane selectively permeable to permit the passage of free ions therethrough while preventing movement of said compound thereacross, wherein in use, said buffering ions bond with said hydrogen ions to produce water and carbon dioxide molecules.

11. An apparatus as claimed in claim 10 further comprising means for extracting a quantity of blood from said patient to said housing for buffering by said compound, and means for reintroducing buffered blood into said patient.

12. A syringe for use in buffering excess hydrogen ions in a patient's blood, said syringe comprising, a housing having a reaction chamber and a blood chamber, a hydrogen ion buffering composition comprising $Ag_2CO_3$ and a resin disposed in said reaction chamber, said buffering composition for bonding with free chloride ions naturally present in said blood and substituting therefor buffering ions selected from the group consisting of carbonate ions and bicarbonate ions, said reaction chamber separated from said blood chamber by a membrane disposed across said housing and selectively permeable to permit the movement of free ions therethrough while preventing movement of said composition thereacross, means for drawing a quantity of said blood from said patient into said housing and then reintroducing said blood into said patient, wherein in use, said buffering ions bond with said hydrogen ions to produce water and carbon dioxide molecules.

\* \* \* \* \*